(12) United States Patent
Milligan

(10) Patent No.: US 11,980,644 B2
(45) Date of Patent: May 14, 2024

(54) METHOD OF INGESTING SUPPLEMENTS IN CONNECTION WITH AN AIRPLANE FLIGHT

(71) Applicant: Jet Renewal Kit, LLC, Fountain Hills, AZ (US)

(72) Inventor: Patti Tveit Milligan, Fountain Hills, AZ (US)

( * ) Notice: Subject to any disclaimer, the term of this patent is extended or adjusted under 35 U.S.C. 154(b) by 173 days.

(21) Appl. No.: 17/155,026

(22) Filed: Jan. 21, 2021

(65) Prior Publication Data

US 2021/0228654 A1 Jul. 29, 2021

Related U.S. Application Data

(60) Provisional application No. 62/964,991, filed on Jan. 23, 2020.

(51) Int. Cl.
| | |
|---|---|
| *A61K 35/742* | (2015.01) |
| *A23L 29/00* | (2016.01) |
| *A23L 33/105* | (2016.01) |
| *A23L 33/18* | (2016.01) |
| *A61K 31/7028* | (2006.01) |
| *A61K 36/31* | (2006.01) |
| *A61K 36/534* | (2006.01) |
| *A61K 36/752* | (2006.01) |
| *A61K 36/9068* | (2006.01) |
| *A61K 38/06* | (2006.01) |

(52) U.S. Cl.
CPC .......... *A61K 35/742* (2013.01); *A23L 29/055* (2016.08); *A23L 33/105* (2016.08); *A23L 33/18* (2016.08); *A61K 31/7028* (2013.01); *A61K 36/31* (2013.01); *A61K 36/534* (2013.01); *A61K 36/752* (2013.01); *A61K 36/9068* (2013.01); *A61K 38/063* (2013.01)

(58) Field of Classification Search
CPC .. A61K 35/742; A61K 31/7028; A61K 36/31; A61K 36/534; A61K 36/752; A61K 36/9068; A61K 38/063; A61K 35/741; A61K 45/06; A23L 29/055; A23L 33/105; A23L 33/18; A23L 33/135; A23L 33/175
See application file for complete search history.

(56) References Cited

U.S. PATENT DOCUMENTS

2021/0220414 A1* 7/2021 Lurye ................. A61K 31/353

OTHER PUBLICATIONS

"Radiation from Air Travel" Centers for Disease Control and Prevention, available at: https://www.cdc.gov/nceh/radiation/air_travel.html, last accessed Mar. 1, 2021, 2 pages.
Boddupalli et al. "Induction of phase 2 antioxidant enzymes by broccoli sulforaphane: perspectives in maintaining the antioxidant activity of vitamins A, C, and E" Frontiers in Genetics, vol. 3, Article 7, (Jan. 24, 2012), 15 pages.
Cosseau et al. "The Commensal Streptococcus salivarius K12 Downregulates the Innate Immune Responses fo Human Epithelial Cells and Promotes Host-Microbe Homeostasis" American Society for Microbiology, Infection and Immunity, vol. 76, No. 9, (Sep. 2008), p. 4163-4175.
Gholami et al. "Effect of stress, anxiety and depression on unstimulated salivary flow rate and xerostomia" Journal of Dental Research, Dental Clinics, Dental Prospects 2017, vol. 11, No. 4, (Aug. 8, 2017), p. 247-242.
Michaelis et al. "Aerotoxic syndrome: a new occupational disease? (adverse health effects experienced by aircrew exposed to aircraft contaminated air)" Occupational & Envionmental Medicine, vol. 75, Issue 2, 1718c, (Apr. 24, 2018), p. A15.
Tiralongo et al. "Elderberry Supplementation Reduces Cold Duration and Symptoms in Air-Travellers: A Randomized, Double-Blind Placebo-Controlled Clinical Trial" Nutrients 2016, vol. 8, No. 4, (Mar. 24, 2016), 15 pages.
Ulbricht et al. "An evidence-based systemic review of elderberry and elderflower (*Sambucus nigra*) by the Natural Standard Research Collaboration" Journal of Dietary Supplements, vol. 11, 2014, Issue 1, (Jan. 10, 2014), p. 80-120.

* cited by examiner

*Primary Examiner* — Aaron J Kosar
(74) *Attorney, Agent, or Firm* — Intellectual Strategies (57) ABSTRACT

A method includes ingesting a first portion of a first supplement within three hours prior to boarding an airplane for a flight and ingesting a first portion of a second supplement within three hours prior to boarding an airplane for a flight. The method includes ingesting a second portion of the second supplement and ingesting a first portion of a third supplement during the flight. The method includes ingesting a second portion of the first supplement alongside a second portion of the third supplement within three hours of the airplane landing. The first supplement includes a probiotic. The second supplement includes an amount of at least one of gluconate, sorbitol, xylitol, maltodextrin, peppermint oil, lemon oil, lime oil, stevia leaf extract, ginger extract, steric acid, or probiotic. The third supplement includes at least one of glutathione, *Brassica Oleracea* sprouts, glucosinolates, glucoraphanin, or rice flour.

9 Claims, 3 Drawing Sheets

METHOD OF INGESTING SUPPLEMENTS IN CONNECTION WITH AN AIRPLANE FLIGHT

CROSS REFERENCE TO RELATED APPLICATION

This application claims the benefit of U.S. Provisional Application No. 62/964,991, filed on Jan. 23, 2020, which is incorporated by reference herein in its entirety.

FIELD

This invention relates to jet lag reduction and more particularly relates to systems and methods for helping a body reduce and adjust to the symptoms jet lag in individuals.

BACKGROUND

Over the past decade, air travel has increased greater than 8% annually. Demand for air travel over the next decade is thought to accelerate. The International Air Transport Association (IATA) expects 7.2 billion passengers to travel in 2035. 82% of travelers dread their travels due to how they feel during and when they arrive at their destination.

Jet lag is a recognized sleep disorder that is experienced after rapid travel across differing time zones. Jet lag may be defined as a condition that is characterized by various psychological and physiological effects (as fatigue and irritability), which occur following long flight through several time zones, and probably results from disruption of circadian rhythms in the human body—also called jet fatigue. The field of aeronautical medicine often refers to jet lag as the biological cost of travel.

Jet lag affects a large proportion of travelers who cross multiple time zones. It is associated with impaired daytime function and general malaise. Jet lag may include other somatic complaints such as gastrointestinal disruption in the days immediately following travel. There is also strong evidence that mood and cognition are adversely affected by jet lag. It is the result of the body's circadian rhythms being out of phase with the new local time zone, among other causes. Experiencing more than one symptom at the same time is often referred to as "jet lag soup." Jet lag symptoms usually persist a day or more until the body realigns its circadian clock, regardless of direction traveled.

The negative effects of jet lag include nervous system aggravation, changes in physiologic organ function, and circadian rhythm disruption. Cabin pressurization, humidity changes, low oxygen levels, and restricted movement in the assigned space creates the perfect storm for a host of symptoms. Symptoms may include but are not limited to one or more of the following: dizziness, fatigue, brain fog, swollen joints, gastrointestinal disturbances, taste bud changes, and even decreased general satiety with foods. Studies have shown that around 90% of travelers experience one or more of these effects of jet lag.

Frequent travelers commented they often "dread" the thought of traveling. They have experienced negative thinking (also known as rumination) about impending jet lag symptoms and anticipation of NOT feeling their best upon arrival. It has been found rumination can add to the stress of travel and specifically intensify the "fight or flight reaction" in the body. These thoughts cause an Autonomic Nervous System (ANS) imbalance and exacerbate the disruptions to the digestive system, specifically a reduction in saliva production. Reducing rumination could lower the stress response especially during travel. In combatting jet lag, travelers spend on average $370 in search of remedies. These range from books to audiotapes, specific therapies, over-the-counter pills and acupressure solutions, all in hopes of easing jet lag symptoms.

Public health officials are similarly worried about the wider effect jet lag can have on individuals who travel frequently. There is a strong correlation to several degenerative diseases such as obesity, diabetes, heart disease, cancer and even cognitive decline.

SUMMARY

The subject matter of the present application has been developed in response to the present state of the art, and in particular, in response to the problems and disadvantages associated with conventional systems that have not yet been fully solved by currently available techniques. Accordingly, the subject matter of the present application has been developed to provide embodiments that overcome at least some of the shortcomings of prior art techniques. In various embodiments, systems and methods are disclosed for reducing the effects of jet lag and assisting the body to reset and synchronize the ANS "rest and digest" system.

Disclosed herein is a method. The method includes ingesting a first portion of a first supplement within three hours prior to boarding an airplane for a flight and ingesting a first portion of a second supplement alongside the first portion of the first supplement, wherein the first portion of the second supplement comprises a probiotic. The method includes ingesting a second portion of the second supplement alongside a first portion of a third supplement during the flight. The method includes ingesting a second portion of the first supplement alongside a second portion of the third supplement within three hours of the airplane landing. The preceding subject matter of this paragraph characterizes example 1 of the present disclosure.

The second supplement further comprises at least one of: lemon oil, peppermint oil, or ginger extract. The preceding subject matter of this paragraph characterizes example 2 of the present disclosure, wherein example 2 also includes the subject matter according to example 1, above.

The first supplement comprises elderberry. The preceding subject matter of this paragraph characterizes example 3 of the present disclosure, wherein example 3 also includes the subject matter according to any one of examples 1-2, above.

The probiotic comprises at least one of: *Bacillus coagulans,* or *Streptococcus salivarius*. The preceding subject matter of this paragraph characterizes example 4 of the present disclosure, wherein example 4 also includes the subject matter according to any one of examples 1-3, above.

The probiotic is *Streptococcus salivarius,* wherein the *Streptococcus salivarius* is at least 1 to 100 billion cfus. This will also support both an immune and digestive system. The preceding subject matter of this paragraph characterizes example 5 of the present disclosure, wherein example 5 also includes the subject matter according to any one of examples 1-4, above.

The third supplement further comprises at least one of: glutathione, glucosinolates, or glucoraphanin. The preceding subject matter of this paragraph characterizes example 6 of the present disclosure, wherein example 6 also includes the subject matter according to any one of examples 1-5, above.

The third supplement comprises *Brassica oleracea* sprouts. The preceding subject matter of this paragraph characterizes example 7 of the present disclosure, wherein example 7 also includes the subject matter according to any one of examples 1-6, above.

The *Brassica oleracea* sprouts are at least 5 to 1000 mg. The preceding subject matter of this paragraph characterizes example 8 of the present disclosure, wherein example 8 also includes the subject matter according to any one of examples 1-7, above.

Ingesting the first portion of the first supplement and the first portion of the second supplement within three hours prior to boarding the flight is configured to bolster an immune system to combat a climate of the airplane. The preceding subject matter of this paragraph characterizes example 9 of the present disclosure, wherein example 9 also includes the subject matter according to any one of examples 1-8, above.

Ingesting the first portion of the second supplement alongside the first portion of the third supplement during the flight is configured to maintain saliva production during the flight to combat dry mouth. The preceding subject matter of this paragraph characterizes example 10 of the present disclosure, wherein example 10 also includes the subject matter according to any one of examples 1-9, above.

The first supplement further comprises at least one first probiotic. The preceding subject matter of this paragraph characterizes example 11 of the present disclosure, wherein example 11 also includes the subject matter according to any one of examples 1-10, above.

Disclosed herein is system for helping a body adjust to or reduce the symptoms of jet lag. The system for helping the body reduce or adjust to the symptoms of jet lag includes at least two portions of a first supplement and at least two portions of a second supplement. A first portion of the second supplement is configured to be taken by a user alongside a first portion of the first supplement between one and three hours prior to boarding an airplane for a flight. The system further includes at least two portions of a third supplement, wherein a first portion of the third supplement is configured to be taken by the user alongside a second portion of the second supplement during the flight. The preceding subject matter of this paragraph characterizes example 12 of the present disclosure.

A second portion of the first supplement is configured to be taken by the user alongside a second portion of the third supplement after landing of the airplane. The preceding subject matter of this paragraph characterizes example 13 of the present disclosure, wherein example 13 also includes the subject matter according to example 12, above.

The first supplement comprises elderberry extract. The preceding subject matter of this paragraph characterizes example 14 of the present disclosure, wherein example 14 also includes the subject matter according to any one of examples 12-13, above.

The second supplement comprises at least one probiotic. The preceding subject matter of this paragraph characterizes example 15 of the present disclosure, wherein example 15 also includes the subject matter according to any one of examples 12-14, above.

The at least one probiotic is *Streptococcus salivarius*, wherein the *Streptococcus salivarius* is at least 1 to 100 billion cfus. The preceding subject matter of this paragraph characterizes example 16 of the present disclosure, wherein example 16 also includes the subject matter according to any one of examples 12-15, above.

The second supplement comprises at least one of: lemon oil, peppermint oil, or ginger extract. The preceding subject matter of this paragraph characterizes example 17 of the present disclosure, wherein example 17 also includes the subject matter according to any one of examples 12-16, above.

The first portion of the first supplement and the first portion of the second supplement are packaged together, the second portion of the second supplement and the first portion of the third supplement are packaged together, and the second portion of the first supplement and the second portion of the third supplement are packaged together. The preceding subject matter of this paragraph characterizes example 18 of the present disclosure, wherein example 18 also includes the subject matter according to any one of examples 12-17, above.

Disclosed herein is a method. The method includes ingesting a first supplement prior to boarding an airplane and after the airplane has landed, wherein the first supplement comprises elderberry. The method includes ingesting a second supplement prior to boarding the airplane and during flight of the airplane, wherein the second supplement is a probiotic, wherein the second supplement comprises *Streptococcus salivarius*. The method includes ingesting a third supplement during the flight and after the airplane has landed, wherein the third supplement is a brocco-glutathione capsule. The preceding subject matter of this paragraph characterizes example 19 of the present disclosure.

The first supplement and the second supplement are taken within three hours of boarding the airplane. The first supplement and the third supplement are taken within three hours of the airplane landing. The preceding subject matter of this paragraph characterizes example 20 of the present disclosure, wherein example 20 also includes the subject matter according to example 19, above.

In some embodiments, a system may include packaging of compounds and instructions for use of the system by a user. Specifically, amounts of a first and second compound may be packaged together alongside instructions for use. Amounts of the first and a third compound may similarly be packaged together with instructions for use. The system may also include amounts of the second and third compounds packaged together with instructions for use.

One embodiment of a method or system includes ingesting saliva-producing foods and beverages during travel, ingesting specific nutrients to support both saliva production and immune system, while performing deep breathing and relaxation techniques to ease the neurological strain during air travel.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

Figure 1:
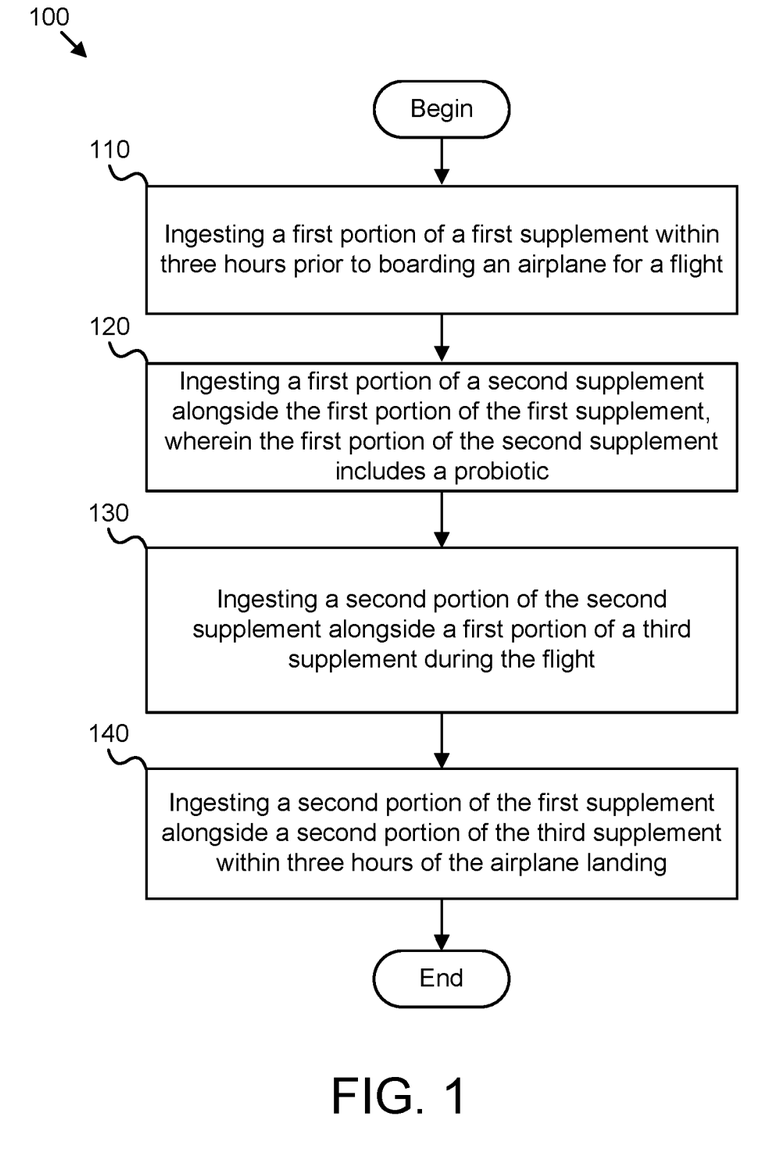
FIG. 1 is a flow chart diagram of a method for stimulating saliva production in accordance with one or more embodiments of the present invention.
Figure 2:
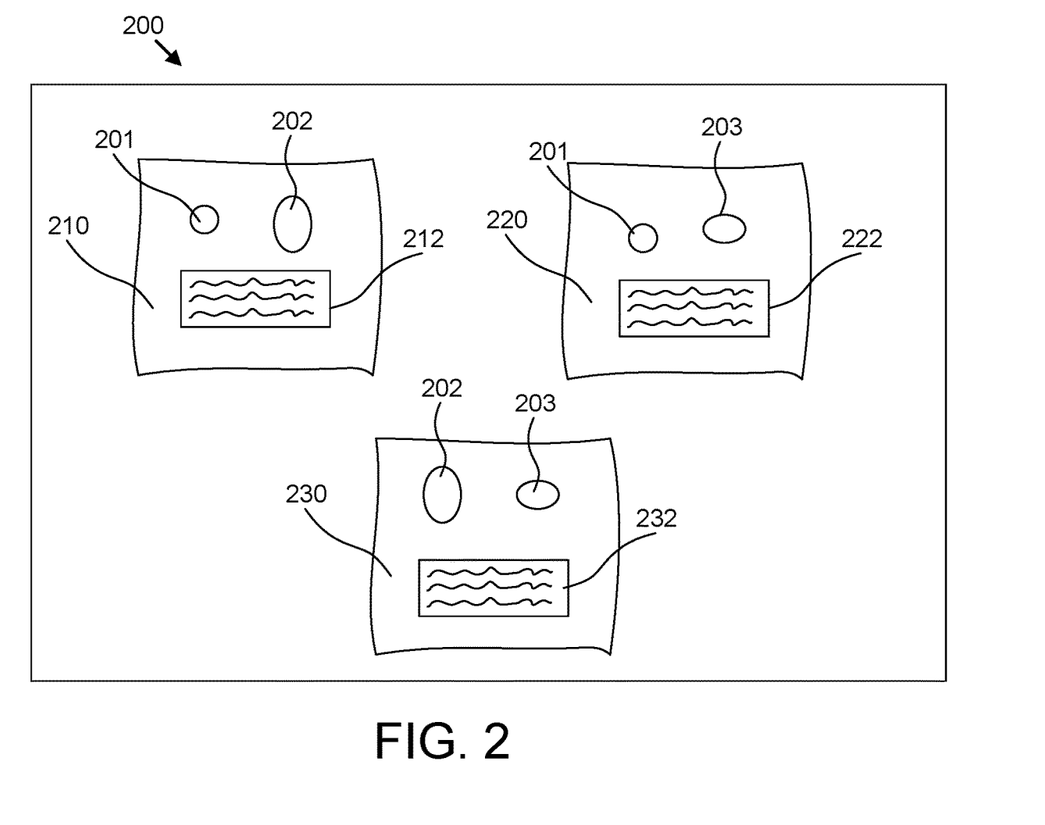
FIG. 2 is a schematic diagram illustrating an embodiment of a system for assisting a body to adjust to and reduce the symptoms of jet lag in accordance with one or more embodiments of the present invention.

Referring now to FIGS. 1 and 2, depictions of specific examples and embodiments of the invention are described herein to teach those skilled in the art how to make and use the invention. For the purpose of teaching inventive principles, some conventional aspects have been simplified or omitted. Those skilled in the art will appreciate variations from these embodiments that fall within the scope of the invention. Those skilled in the art will appreciate that the features described below can be combined in various ways to form multiple embodiments and variations of the invention. As a result, the invention is not limited to the specific embodiments described below, but only by the claims and their equivalents.

The World Health Organization (WHO) currently offers an approach to avoiding jet lag. The conventional approach focuses on pre-emptively aligning the body's circadian rhythm with the end-destination's time zone. This means changing eating times and sleeping times to match what they will be in the end destination. A second approach to avoiding jet lag involves altering one's diet a few days prior to departure. The technique involves rotations of feasting and fasting to prepare the body for flight.

While these techniques have been tested, the results are inconsistent from traveler to traveler. Changes to the diet must also be implemented ahead of time, requiring a fair amount of planning. Additionally, both approaches offer little to no specifics for travelers and may be difficult to implement. Alongside these problems, established methods for adjusting to the symptoms of jet lag have failed to account for the role saliva plays in boosting the immune and digestive systems and mitigating the effects of jet lag. What is needed is a low-cost, simple yet detailed process to reduce the symptoms of jet lag.

A typical human produces between 1-2 liters of saliva daily in a typical environment. Saliva is a vital fluid for survival and plays a key role in both digestive and immune functions. In addition, saliva adds to the pleasure and sensory appreciation of foods and eating experiences. Producing enough saliva is part of the autonomic nervous system (ANS) "relax and digest" function. When a human is stressed or neurologically challenged, saliva production is dramatically reduced. Saliva production drops as much as 30-50% of normal production during air travel.

Reduced saliva production is also seen as a growing medical issue. Dry mouth, or xerostomia, refers to a condition in which there is not enough saliva to keep the mouth wet. Dry mouth is becoming a major issue from functional, psychological and social impact perspectives as people age and undergo a variety of treatments for health conditions, i.e., cancer. It is of great concern as it clearly changes the desire and enjoyment of foods. Once someone is impacted in this way, we see changes in their health and most importantly, their quality of life.

Not having enough saliva can cause a host of chronic health issues, including increased plaque, tooth decay, gum disease, mouth sores, yeast infection (thrush), cracked lips and even poor nutrition often resulting in problems chewing and swallowing. Decreased saliva can also lead to a lack of general satiety with foods, resulting in less food consumed after travel further exacerbating the consequences of poor nutrition.

Saliva production is greatly affected when we are dehydrated or neurologically challenged (stressed) as in staying in the body's "fight or flight" mode. Saliva is needed to keep the mucous membranes in our mouth moist and is one of the first lines of defenses of the immune system. Saliva is essential for the eating process, not only to moisten food for chewing and swallowing, but also for the taste buds to detect and analyze the architecture (i.e., aromas and flavors) of foods. The salivary glands are involved at all levels of eating. Secretions from the salivary glands are controlled by our ANS and flow well when in "rest and digest" vs. "fight or flight" mode. The liters of saliva you produce every day contain antibacterial properties, which guard against infections and nourish gums and teeth. May sound strange, but saliva plays a key role during travel to defend and render inactive the host of new and different microbes that are introduced with air travel.

When our neurological system is challenged (as in flying), the amount and composition of saliva changes. We produce thicker, mucous saliva when our ANS neurological system feels threatened or when perception of fear, stress or anger is aroused. A drop in saliva could be a signal to the digestive system to take a pause in functioning.

Certain foods and spices stimulate salivary glands and, as a result, increase saliva production. They are called "sialagogue" foods and may be consumed in addition to the methods described herein. Some examples are foods such as apples, lemon or tomato juices, and high-water content vegetables such as celery, carrots, etc. Spices such as ginger, cardamom and cayenne pepper along with dried goji and tart cherries are a few examples of spices which stimulate salivary glands. The present application discloses a protocol and various embodiments designed to aid the body's immune system and increase saliva production. One embodiment of a protocol includes saliva-producing foods and beverages during travel, ingesting specific nutrients to support both saliva production and the immune system, while performing deep breathing and relaxation techniques to ease the neurological strain during air travel.

Disclosed herein is a method. In an embodiment, the method includes ingesting a chewable probiotic tablet alongside an elderberry probiotic capsule prior to boarding an airplane for a flight. Ingestion of the chewable probiotic tablet with the elderberry capsule is configured to boost both an immune and digestive system of a body. The chewable tablet is taken by mouth and includes *Streptococcus salivarius* to support oral immune health and saliva production. The chewable tablet may further include peppermint and lemon essential oils, and ginger root extract. The chewable tablet is configured to support saliva retention and keep the nervous system calm. The elderberry capsule includes elderberry extract and/or the probiotic *Sambucus nigra*.

The method includes ingesting the chewable probiotic tablet alongside a brocco-glutathione capsule during the flight. Ingestion of the chewable probiotic tablet with the brocco-glutathione capsule is configured to support the immune system and build the body's defenses. The chewable tablet may be taken by mouth. The brocco-glutathione capsule may be taken with water and includes *brassica oleracea* (organic broccoli) sprouts, glutathione and glucoraphanin (sulforaphane glucosinolate).

The method further includes ingesting the elderberry capsule alongside the brocco-glutathione capsule upon landing of the flight or a short time thereafter (within one to three hours of the flight landing). Ingestion of the elderberry and brocco-glutathione capsules is configured to support immune, digestive metabolism and cellular detoxification. Both capsules may be taken with water. In some embodiments of the method, the elderberry capsule includes mushroom extract blends. In some embodiments of the method, instead of the elderberry capsule a combination of one or more of vitamin C, zinc, or vitamin A may be taken.

Referring now to FIG. 1, a method 100 for stimulating saliva production is disclosed. The method 100 includes, at block 110, ingesting a first portion of a first supplement within three hours prior to boarding an airplane for a flight. The method 100 includes, at block 120, ingesting a first portion of a second supplement alongside the first portion of the first supplement, wherein the first portion of the first supplement comprises a probiotic. The method 100 includes, at block 130, ingesting a second portion of the second supplement alongside a first portion of a third supplement during the flight. In some embodiments, the first portion of the third supplement comprises *brassica oleracea* sprouts. The method 100 includes, at block 140, ingesting a second portion of the first supplement alongside a second portion of the third supplement within three hours of the airplane landing. The method then ends.

In some embodiments, ingesting alongside may mean ingesting simultaneously or substantially simultaneously. In some embodiments, ingesting alongside may mean ingesting consecutively (e.g., one right after the other). In some embodiments, ingesting alongside may mean ingesting within a specified time period such as within one minute, two minutes, five minutes, or fifteen minutes.

In some embodiments, the first portion and the second portion of the first supplement are the same. In some embodiments, the first portion of the first supplement is larger than the second portion of the first supplement. In some embodiments, the first portion of the first supplement is smaller than the second portion of the first supplement.

In some embodiments, the first portion and the second portion of the second supplement are the same. In some embodiments, the first portion of the second supplement is larger than the second portion of the second supplement. In some embodiments, the first portion of the second supplement is smaller than the second portion of the second supplement.

In some embodiments, the first portion and the second portion of the third supplement are the same. In some embodiments, the first portion of the third supplement is larger than the second portion of the third supplement. In some embodiments, the first portion of the third supplement is smaller than the second portion of the third supplement. Embraced within the scope of this disclosure is any permutation of portion sizes of the three supplements as described in the previous three paragraphs.

In some embodiments, the first portion and the second portion of the first supplement are compositionally the same. In some embodiments, the first portion of the first supplement is compositionally different than the second portion of the first supplement. In some embodiments, the first portion and the second portion of the second supplement are compositionally the same. In some embodiments, the first portion of the second supplement is compositionally different than the second portion of the second supplement. In some embodiments, the first portion and the second portion of the third supplement are compositionally the same. In some embodiments, the first portion of the third supplement is compositionally different than the second portion of the third supplement. Embraced within the scope of this disclosure is any permutation of composition of the three supplements as described in this paragraph.

In some embodiments, the first portion of the first supplement and the first portion of the second supplement are taken at boarding of the airplane or within a short time period prior to boarding. In some embodiments, the time period is one hour. In some embodiments, the time period is two hours. In some embodiments, the time period is three hours. In some embodiments, the time period is one half of an hour. In some embodiments, the time period is one quarter of an hour. In some embodiments, the first portion of the first supplement and the first portion of the second supplement are taken shortly after boarding but before takeoff of the airplane.

In some embodiments, the first supplement may include an amount of Elderberry (*Sambucus nigra*) fruit extract, standardized to 35 mg anthocyanidins. The *Sambucus nigra* may include concentrated fruit extract (standardized to 13%) (made from 32,000 mg of fresh elderberries). In some embodiments, the first supplement may include 1-1200 mg of *Sambucus nigra*, more particularly 20-600 mg, even more particularly 50-30 mg. First supplement may be standardized to 25 mg of anthocyanidins at 275 mg of *Sambucus*

*nigra*. In one embodiment, the first supplement may include the composition sold under the tradename Nature's Answer® Sambucus+Probiotic™). In another embodiment, the first supplement may be standardized to 2.5 billion cfu.

The second supplement may include an amount of zinc gluconate, sorbitol, xylitol, maltodextrin, peppermint oil, lemon oil, lime oil, stevia leaf extract, ginger extract, and/or steric acid, oral probiotics, a probiotic composition sold under the tradename BLIS M18®, and/or combinations thereof. The second supplement may include, or be in the form of, a dry mouth lozenge. In a specific embodiment, the second supplement may include a dry mouth lozenge composition sold under the tradename Nature's Answer® Perio-Brite® Dry Mouth Lozenges.

In some embodiments, second portion of the second supplement and the first portion of the third supplement are taken during the flight. In some embodiments, they are taken any time between takeoff of the plane and landing of the plane. In some embodiments, the second supplement includes an antioxidant. In some embodiments, the second supplement may include glutathione.

The third supplement may include glutathione, *Brassica oleracea* sprouts, glucosinolates, glucoraphanin, and/or combinations thereof. In an embodiment, second supplement may include from 5 to 1000 mg of reduced form glutathione, more particularly 100-500 mg, even more particularly 200-300 mg glutathione. In an embodiment, second supplement may also include 5-1000 mg of *Brassica oleracea* sprouts, more particularly 100-500 mg, even more particularly 200-300 mg of *Brassica oleracea* sprouts. In an embodiment, second supplement may also include 5-1000 mg of glucosinolates, more particularly 100-500 mg, even more particularly 200-300 mg glucosinolates. In an embodiment, second supplement may include 5-1000 mg of glucoraphanin, more particularly 100-500 mg, even more particularly 200-300 mg glucoraphanin.

In some embodiments, the third supplement may also include rice flour. In an embodiment, the second supplement may include a glutathione-and-broccoli composition, for example the glutathione-and-broccoli sprouts composition sold under the tradename Nature's Answer® Brocco-Glutathione™ which combines a formulation of reduced L-glutathione composition sold under the tradename Setria® with an organic broccoli sprouts composition sold under the tradename HiActives®. These two ingredients are natural sources of antioxidants that deliver protection at a cellular level.

In some embodiments, the method includes ingesting an amount of the second supplement and an amount of the third supplement while the airplane is in flight, and generally after the ingesting 110. In some embodiments, the second supplement may also include probiotics, such as *Bacillus coagulans* and *Streptococcus salivarius*. The probiotic *Streptococcus salivarius* supports oral immune health and saliva production in a user. In some embodiments, the second supplement may include 1-100 billion colony forming units ("cfu") of one or more probiotics, more particularly 1-50 Billion cfu, even more particularly 5-15 billion cfu.

As an example, a method for reducing the effects of jet lag, assisting a body in adjusting to the symptoms of jet lag, and/or increasing saliva of a user includes ingesting an amount of a first and second supplement, ingesting an amount of the second supplement and an amount of a third supplement while the airplane is in flight, and ingesting an amount of the first supplement and an amount of the third supplement upon, or within a short time of, landing of the airplane.

A first ingesting may include ingesting the first and second supplement generally about the time a user gets onto an airplane for a flight or within three hours prior to such time. A second ingesting may include ingesting an amount of the second supplement and an amount of a third supplement while the airplane is in flight, and generally after the first ingesting. A third ingesting may include ingesting an amount of the first supplement and an amount of a third supplement generally after the airplane lands, and generally after the second ingesting.

In some embodiments, the method may include eating 2-3 sialagogue foods within about 2 hours of takeoff of the airplane. Method 100 may also include consuming generally 100-200 milliliters of water per hour of the flight and/or lemon, ginger or fennel teas during flight, while minimizing caffeine, alcohol, and sugary drinks during flight. Method 100 may also include inhaling for 4 seconds, holding breath for 4 seconds, and breathing out for four seconds. Method 100 may also include adjusting posture during flight, which may include keeping the head in line with the spine, and using lower back support. Method 100 may include eating 2-3 sialagogue foods within about 2 hours of landing of the airplane. Method 100 may also include consuming generally 100-200 milliliters of water per hour after landing of the airplane.

Sialagogue foods may include, but are not limited to, apples, lemon juice, tomato juice, coconut water, endive, miso soup, mushroom soup, carrots, celery, cucumbers, cayenne pepper, cumin, ginger, fennel, cardamom, dried cherries, goji berries, prebiotics, and/or probiotics.

FIG. 2 illustrates a system for helping a body adjust to and reduce the symptoms of jet lag, according to one or more embodiments. Although shown and described with certain components and functionality, other embodiments of the system may include fewer or more components to implement less or more functionality.

System 200 includes separate packaging 210, 220, 230 and instructions for use 212, 222, 232 for each packaging. First packaging 210 may include an amount or portion of the first supplement 201 and an amount or portion of the second supplement 202, as well as directions for use 212. Second packaging 220 may include an amount or portion of the second supplement 202 and an amount or portion of the third supplement 203, and directions for use 222. Third packaging 230 may include an amount or portion of the first supplement 201 and an amount or portion of the third supplement 203, and directions for use 232.

In some embodiments, the supplements are as described in the various embodiments associated with FIG. 1. In addition, the directions for use 212, 222, 232 include directions similar to the method steps described in the various embodiments associated with FIG. 1.

System 200 may include additional information regarding ingredients, nutrition information, disclaimers, and certifications for the supplements. Certifications may include made in USA, cruelty-free, GMP certified, non-GMO, gluten-free, location of manufacture, organic, etc. The systems and methods described herein are configured to allow users to experience less brain fog, feel more relaxed during their trip, and have more energy after travel.

Figure 3:
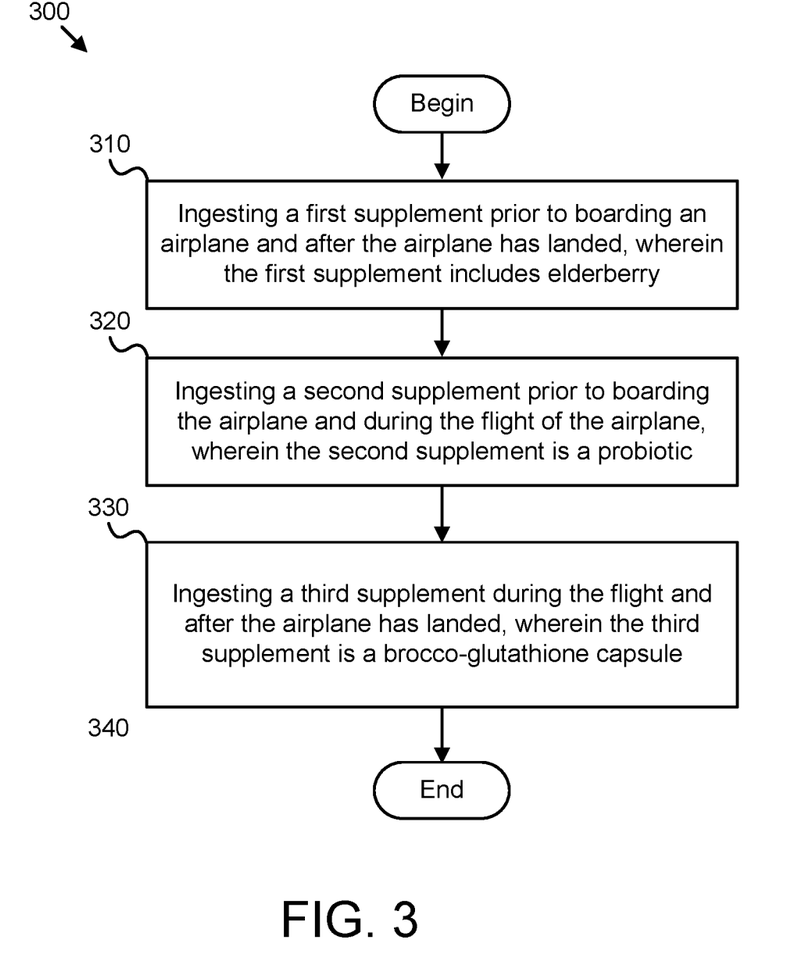
FIG. 3 is a flow chart diagram of a method for assisting a body to adjust to and reduce the symptoms of jet lag in accordance with one or more embodiments of the present invention.

Referring now to FIG. 3, a flow chart diagram of a method 300 is depicted. The method 300 is a sample method for reducing the effects of jet lag, assisting a body in adjusting to the symptoms of jet lag, and/or increasing saliva of a user. The method 300 includes, at block 310, ingesting a first supplement prior to boarding an airplane and after the airplane has landed, wherein the first supplement comprises elderberry.

The method 300 includes, at block 320, ingesting a second supplement prior to boarding the airplane and during flight of the airplane, wherein the second supplement is a probiotic, wherein the second supplement comprises *Streptococcus salivarius*. The method 300 includes, at block 330, ingesting a third supplement during the flight and after the airplane has landed, wherein the third supplement is a brocco-glutathione capsule.

In some embodiments, the second supplement is a chewable probiotic tablet. Ingestion of the chewable probiotic tablet with the brocco-glutathione capsule further boosts the immune system and builds the body's defenses. The chewable tablet is taken by mouth and the brocco-glutathione capsule is taken with water. In some embodiments, the brocco-glutathione capsule includes *Brassica oleracea* (organic broccoli) sprouts, glutathione and glucoraphanin (sulforaphane glucosinolate).

In some embodiments, the chewable tablet includes *Streptococcus salivarius* to support to support immune, digestive metabolism and cellular detoxification. The chewable tablet further includes peppermint and lemon essential oils, and ginger root extract to support saliva retention and keep the nervous system calm. In some embodiments of the method, the elderberry capsule includes elderberry extract and *Sambucus nigra*.

In some embodiments, ingestion of the elderberry and brocco-glutathione capsules supports immune, digestive metabolism and cellular detoxification. Both capsules will be taken with water. In some embodiments of the method, the elderberry capsule includes mushroom extract blends. In some embodiments of the method, in place of an elderberry capsule a combination or one or more of vitamin C, zinc, or vitamin A may be taken.

Although the foregoing disclosure provides many specifics, these should not be construed as limiting the scope of any of the ensuing claims. Other embodiments may be devised which do not depart from the scopes of the claims. Features from different embodiments may be employed in combination. The scope of each claim is, therefore, indicated and limited only by its plain language and the full scope of available legal equivalents to its elements.

In the above description, specific details of various embodiments are provided. However, some embodiments may be practiced with less than all of these specific details. In other instances, certain methods, procedures, components, structures, and/or functions are described in no more detail than to enable the various embodiments of the invention, for the sake of brevity and clarity.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

Although specific embodiments of the invention have been described and illustrated, the invention is not to be limited to the specific forms or arrangements of parts so described and illustrated. The scope of the invention is to be defined by the claims appended hereto and their equivalents.

Reference throughout this specification to features, advantages, or similar language does not imply that all of the features and advantages that may be realized with the subject matter of the present disclosure should be or are in any single embodiment. Rather, language referring to the features and advantages is understood to mean that a specific feature, advantage, or characteristic described in connection with an embodiment is included in at least one embodiment of the present disclosure. Thus, discussion of the features and advantages, and similar language, throughout this specification may, but do not necessarily, refer to the same embodiment.

In the above description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

As used herein, a system, apparatus, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

What is claimed is:

1. A method comprising:
ingesting a first portion of a first supplement within three hours prior to boarding an airplane for a flight, wherein the first supplement comprises a first probiotic;
ingesting a first portion of a second supplement within three hours prior to the boarding the airplane for the flight, wherein the second supplement comprises an amount of at least one of gluconate, sorbitol, xylitol, maltodextrin, peppermint oil, lemon oil, lime oil, stevia leaf extract, ginger extract, steric acid, or a second probiotic;
ingesting a second portion of the second supplement during the flight and ingesting a first portion of a third supplement during the flight, wherein the third supplement comprises at least one of glutathione, *Brassica oleracea* sprouts, glucosinolates, glucoraphanin, or rice flour; and
ingesting a second portion of the first supplement within three hours of the airplane landing and ingesting a second portion of the third supplement within three hours of the airplane landing.

2. The method of claim 1, wherein the first supplement comprises elderberry.

3. The method of claim 1, wherein the first probiotic comprises at least one of: *Bacillus coagulans,* or *Streptococcus salivarius*.

4. The method of claim 1, wherein the first probiotic is *Streptococcus salivarius,* wherein the *Streptococcus salivarius* is at least 1 to 100 billion cfus.

5. The method of claim 1, wherein the third supplement further comprises at least one of: glutathione, glucosinolates, or glucoraphanin.

6. The method of claim 1, wherein the third supplement comprises *Brassica oleracea* sprouts.

7. The method of claim 6, wherein the *Brassica oleracea* sprouts are at least 5 to 1000 mg.

8. The method of claim 1, wherein ingesting the first portion of the first supplement and the first portion of the second supplement within three hours prior to boarding the flight is configured to support an immune system.

9. The method of claim 1, wherein ingesting the first portion of the second supplement alongside the first portion of the third supplement during the flight is configured to maintain saliva production during the flight to combat dry mouth.

* * * * *